United States Patent [19]
Dickert et al.

[11] Patent Number: 4,926,156
[45] Date of Patent: May 15, 1990

[54] APPARATUS FOR MEASURING THE PARTIAL PRESSURE OF GASES OR VAPORS

[75] Inventors: Franz Dickert, Nuernberg; Heinz Kimmel, Buckenhof; Gert Mages, Hemhofen; Sabine Schreiner, Erlangen, all of Fed. Rep. of Germany

[73] Assignee: Siemens Aktiengesellschaft, Berlin & Munich, Fed. Rep. of Germany

[21] Appl. No.: 323,584

[22] Filed: Mar. 14, 1989

[30] Foreign Application Priority Data

Mar. 14, 1988 [DE] Fed. Rep. of Germany ....... 3808470
Mar. 14, 1988 [DE] Fed. Rep. of Germany ....... 3808469

[51] Int. Cl.[5] ............ H01C 10/10
[52] U.S. Cl. ............ 338/36; 338/34; 73/23; 73/29
[58] Field of Search ............ 338/34, 36; 324/65 R; 23/293 R; 422/83, 98; 73/23, 29

[56] References Cited

U.S. PATENT DOCUMENTS 4,333,067 6/1982 Kugimiya et al. ............ 338/34
4,642,601 2/1987 Sugawara et al. ............ 338/34 X
4,651,121 3/1987 Furubayashi et al. ............ 338/34
4,688,015 8/1987 Kojima et al. ............ 338/34

*Primary Examiner*—Bruce A. Reynolds
*Assistant Examiner*—M. M. Lateef
*Attorney, Agent, or Firm*—Kenyon & Kenyon

[57] ABSTRACT

An apparatus comprising a chemically sensitive sensor material, having an electrical resistance or dielectric constant which changes under the effect of the gases or vapors. According to the invention, this sensor material, which comprises either hydrophobic metal complexes, or a mixture of at least one phthalide and at least one acidic compound, serves as resistance or as dielectric material. These sensor materials change their ion mobility and/or their ionic concentration under the effect of gases or vapors, thereby changing their resistance or capacitance. The change in resistance or the change in capacitance can expediently be converted into a frequency change by a multivibrator. Thus, one obtains an especially simple and very effective sensor for gases and vapors.

27 Claims, 3 Drawing Sheets f
[kHz]
110
100
90
80
70
K1
1
2
3
4
5
6
CE[10-1%]

f
[kHz]
47,7
47,5
47,3
47,1
K2
1
5
10
15
CA[10-1%]

APPARATUS FOR MEASURING THE PARTIAL PRESSURE OF GASES OR VAPORS

This application is related to commonly assigned U.S. application Ser. No. 323,345, filed the same day, entitled "Sensor Material for Measuring the Partial Pressure of Gases or Vapors; and Gas Sensor", the disclosure of which is hereby incorporated by reference.

FIELD OF THE INVENTION

The present invention relates to an apparatus for continuously measuring the partial pressure of gases or vapors with a chemically sensitive sensor material. The chemically sensitive sensor material has an electrical resistance or dielectric constant that changes under the effect of the gas or vapor.

BACKGROUND OF THE INVENTION

Generally known sensors for measuring gases and vapors are optical filters containing a sensor material which reversibly changes color in the presence of a gas or vapor. This color change affects the transmittancy of the filter under the influence of the gases or vapors. These filters contain a mixture of an alkaline, or acid, color former, also known as a colorant, and a complementary compound. Triphenylmethane compositions, preferably crystal violet lactone, for example can be utilized as color formers ("colorants"). These filters may also comprise colorants of the triphenylmethane system, preferably phthalein or sulphophthalein, which can be embedded in a matrix and provided with a carrier. The change in the transmittancy of the filter, under the effect of the gases or vapors, is converted into an electric signal and processed electronically. A filter such as generally described above is discussed in German Published Patent Application No. 35 06 686.

Metal complexes having ligands with hydrophobing properties are generally known. Examples of these metal complexes include: monodentate ligands, for example dimethyl formamide; bidentate ligands; chelate ligands, for example ethylenediamine and acetylacetone, podandens and macrocylenes such as crown ethers and cryptands.

A change in electrical properties, such as a change in the dielectric constant or the electrical conductivity of a material, can be utilized to measure, or sense, gases or vapors, see, for example, *Sensorik*, Springer Publishers Heidelberg, 1986, pages 195–199. This effect can be utilized in a simple way, such as with a gas sensor in the form of a condenser, to measure the humidity of the air. In this type of sensor the water-adsorbing dielectric material is applied to metal electrodes. The second electrode of the condenser is applied to the dielectric material, in the form of two engaging finger patterns, to form a comb-like structure. A dielectric material, which changes its dielectric constant under the effect of a gas, is superimposed over this comb-like structure. The corresponding change in the capacitance serves as a sensor signal.

The present invention provides a simple sensor system for gases or vapors, which enables the partial pressure or the concentration of virtually all solvents and gases to be continuously measured, even at low temperatures.

SUMMARY OF THE INVENTION

According to the present invention, a hydrophobic metal complex, or a mixture comprising at least one phthalide and at least one acidic compound, are provided as electric resistance sensor material or as dielectric sensor material in a sensor. Under the effect of gases or vapors, these sensor materials demonstrate a change in ionic concentration or ion mobility. A sensor system for gases or vapors with these sensor materials can be economically designed as a small and easily transportable, hand-operated, instrument. The sensor materials of the present invention also make it possible without undue expertise, to establish the existence of gases and vapors at any location, even at room temperature.

In a preferred embodiment the sensor system further comprises an a stable multivibrator, which converts the change in resistance, or the change of the dielectric constant, into a frequency change.

The sensor material of the present invention at least partially comprises macrocyclic metal complexes, preferably the ligands of the crown ether or cryptand type. For example §-benzo [15] crown-5 or also §-benzocryptand, for example §-5,6-benzo-4,7,13,16,21,24-hexoaxa-1.10-diazobicyclo-(8,8,8 -hexacosan can be selected as ligands. These compounds are known under the designation §-$222_B$. The metal complexes of the present invention preferably comprise a polymer crown ether or cryptand, which coordinates with a variably charged metal ion, such as a sodium ion, $Na^+$; or a potassium ion, $K^+$; or a magnesium ion, $Mg^{++}$. Polymer structures, which can be used to produce stable layers, are preferred.

Macrocyclic metal complexes, with counter ions of variable nucleophiles, preferably chloride anions $Cl^-$ or perchlorate anions $ClO_4^-$ may also be utilized in the present invention.

Compounds suitable for anion or cation solvation, which can therefore stabilize positively or negatively charged particles are suitable co-substances. For example, solid or also polyfunctional alcohols, preferably pyrogallol or etherified polyethylene glycols, are suitable co-substances.

phthalides, preferably substituted phthalides, for example 3-(N-methyl 1-3-indolyl 1)-6-dimethylaminophthalide are also suitable for use in the present invention. Also suited are 3,3-diphenylphthalides, for example 3-(p-dimethylaminophenyl)-3-(p-methoxyphenyl)-6-dimethyl aminophthalide or 3,3-bis(p-dimethylaminophenyl)-6-dimethylaminophthalide, which is known under the designation crystal violet lactone.

Preferable acidic co-substances are phenolic acids, preferably 2,2-(4-hydroxyphenyl)-propane, which is sold commercially under the designation "Bisphenol-A", or hydroxy-(phenyl)-bis(p-hydroxyphenyl)-methane, which is sold commercially under the designation "Benzaurin".

Suitable transparent supporting materials include glass and plastics. The sensor-active material may also be embedded in a matrix. Inorganic and organic polymer substances, such as polyvinyl chloride, silicons and collodion, and polymers with active functional groups, which are suited for cation and anion solvation, are suitable matrix materials.

DETAILED DESCRIPTION OF THE INVENTION

Figure 1:
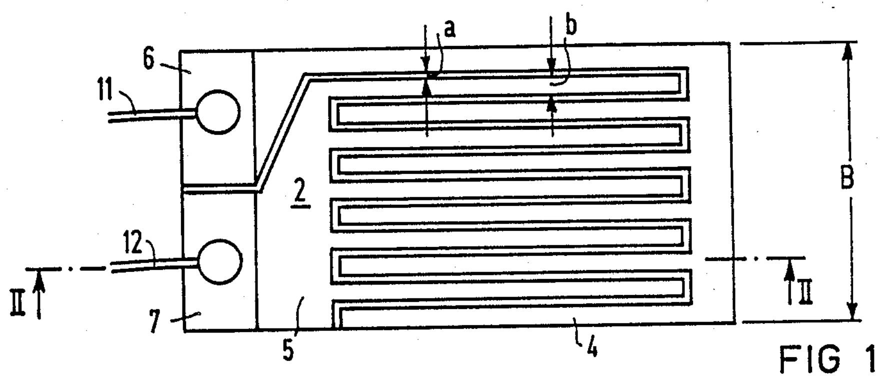
FIG. 1 shows an embodiment of the present invention in a schematic top view.
Figure 2:
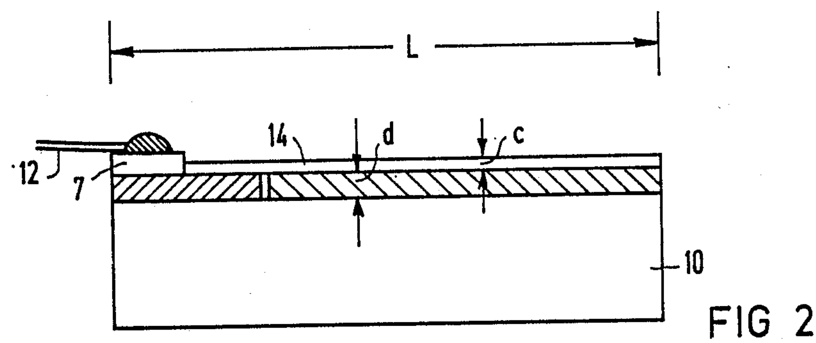
FIG. 2 shows a side view of the embodiment shown in FIG. 1.

In the embodiment of the present invention shown in FIG. 1, a gas sensor 2 has two electrodes, 4 and 5 respectively, are arranged in a comb-like structure, with engaging teeth, on a substrate, 10 with a length L of approximately 40 mm and a width B of approximately 8 mm shown in the side view of FIG. 2. Substrate 10 can be made of glass. Electrodes 4 and 5 have large-surface ends adapted to connect electric conductors. For this purpose, electrodes 4 and 5 may be furnished with additional metal coatings 6 and 7, which may be copper. An electric supply lead, 11 or 12, respectively, is attached, by soldering, to each metal coating. The band-shaped teeth of the comb-like structure of both electrodes, not shown in great detail in the figure, are arranged at a slight distance "a" from each other. The distance "a" may be between approximately 10 and approximately 50 μm. The width "b" of the band-shaped teeth may be between approximately 100 and approximately 200 μm.

A predetermined quantity of a solution containing the sensor material is applied dropwise onto the comb-like structure of both electrodes 4 and 5 and the solvent is evaporated. Electrodes 4 and 5 have a thickness "d", shown in FIG. 2, up to about 0.5 μm. Thereby, a cohesive sensor layer is formed with a thickness "c", selected to be at least large enough to avoid an island formation. Thickness "c" therefore, preferably amounts to at least 50 nm and, in general, does not significantly exceed 2 mm. Metal coating 7, with its supply lead, 12, is also depicted in FIG. 2. The change in the capacitance, or the resistance, of the sensor layer 14, in response to a gas or vapor, serves as an output signal for the gas sensor 2.

Figure 3:
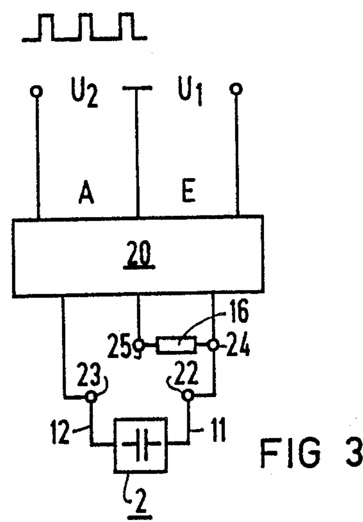
FIG. 3 shows an electrical schematic of a multivibrator.

In another embodiment of the sensor system of the present invention, the change in the resistance, or the capacitance, of the sensor layer 14 can be converted into a frequency change. For this purpose, an a stable multivibrator 20 as shown in FIG. 3, can be provided. Input E, of this a stable multivibrator, may be connected to a circuit voltage $U_1$ equal to 5 V. To measure the change in the capacitance of the sensor layer 14 of the sensor 2, the supply leads 11 and 12 of the sensor 2 are connected to the multivibrator supply terminals designated 22 and 23. In the form of this embodiment with capacitance measurement, a ground resistor 16 is inserted between two additional terminals 24 and 25. As a result of the capacitance change in the sensor layer 14 of the sensor 2, a corresponding frequency change in the output voltage $U_2$ is obtained at the output A of the multivibrator 20. In the case of the embodiment of a sensor layer 14, whereby its change in resistance serves as a signal, a ground capacitor is connected between the terminals 22 and 23 of the multivibrator 20, and the sensor 2, with its supply leads 11 and 12, is connected between the terminals 24 and 25.

Figure 4:
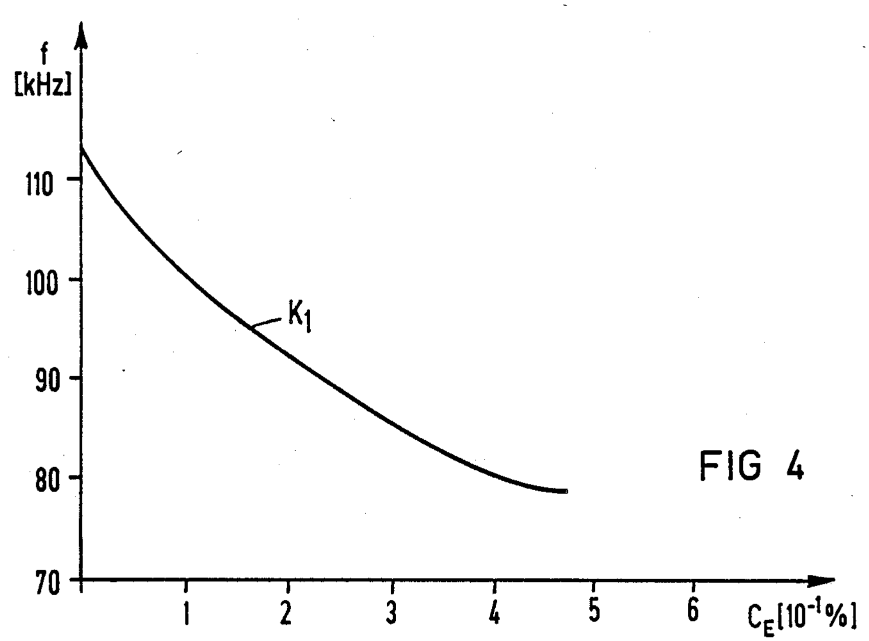
FIG. 4 is a graph plotting the frequency, in kilohertz, with respect to the concentration of ethanol for an embodiment of the present invention.

In the embodiment of the sensor 2, in which resistance is measured, a macrocyclic metal complex, with good electric conductivity, can be applied as resistance material to form a sensor layer 14. This can be a complex comprising potassium chloride and polymer crown ether §-B[15]K-5. To measure, for example, the ethanol concentration of air with a 50% moisture content, one obtains, a frequency, at output A of the multivibrator 20 according to the characteristic curve K1 of FIG. 4. In FIG. 4, the frequency "f" in KHz is plotted with respect to the ethanol concentration $C_E$ in $10^{-1}$%. An appropriate measuring instrument may be calibrated according to the characteristic curve $K_1$.

Figure 5:
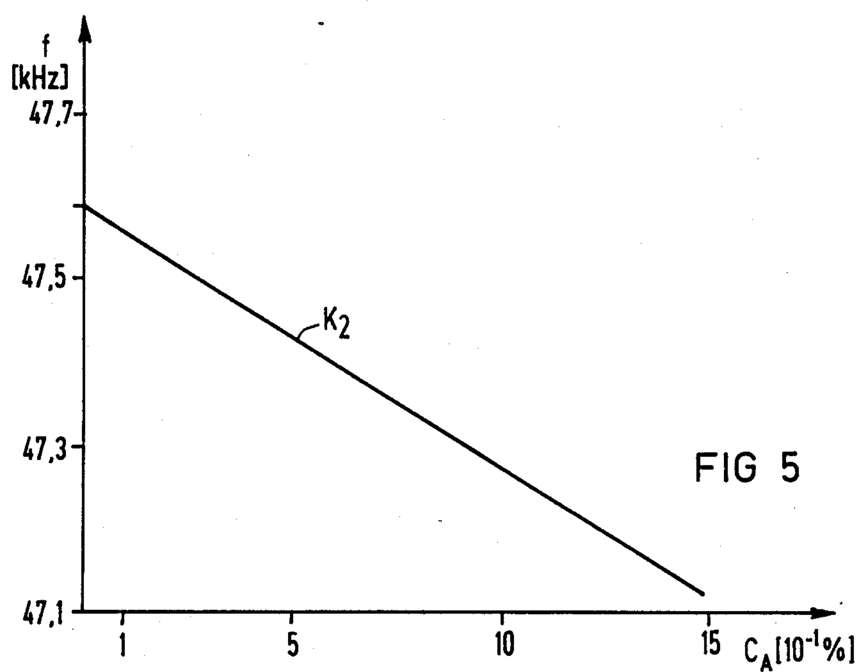
FIG. 5 is a graph plotting the frequency, in kilohertz, with respect to acetone concentration for an embodiment of the present invention.

In the embodiment of the sensor 2 in which capacitance is measured sensor layer 14 may comprise a substitute 3,3-diphenylphthalide,

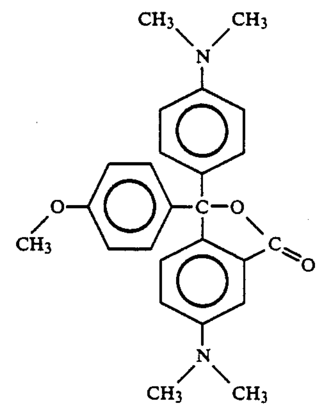

with bisphenol-A (1:4) as a co-substance, according to the following description. This mixture demonstrates a relatively high resistance and serves as a dielectric in the measurement setup. The diagram of FIG. 5 shows the frequency, in KHz of the multivibrator 20 as a function of acetone concentration $C_A$ in $10^{-1}$%. $K_2$ of FIG. 5 shows the characteristic frequency curve for the acetone concentration of air with a 50% moisture content. An appropriate measuring instrument may be calibrated according to the characteristic curve $K_2$.

Figure 6:
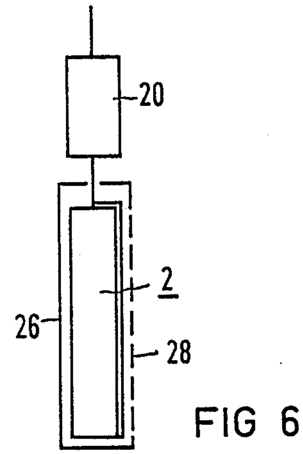
FIG. 6 shows an immersion sensor according to the present invention.

The system with the basic unit from the sensor 2, and with the multivibrator 20, can also be designed as an immersion sensor, as shown in FIG. 6. In this embodiment the sensor is provided with a chamber 26, having an inner wall at least partially comprising a gas permeable membrane, 28, shown with a dotted line in FIG. 6.

Figure 7:
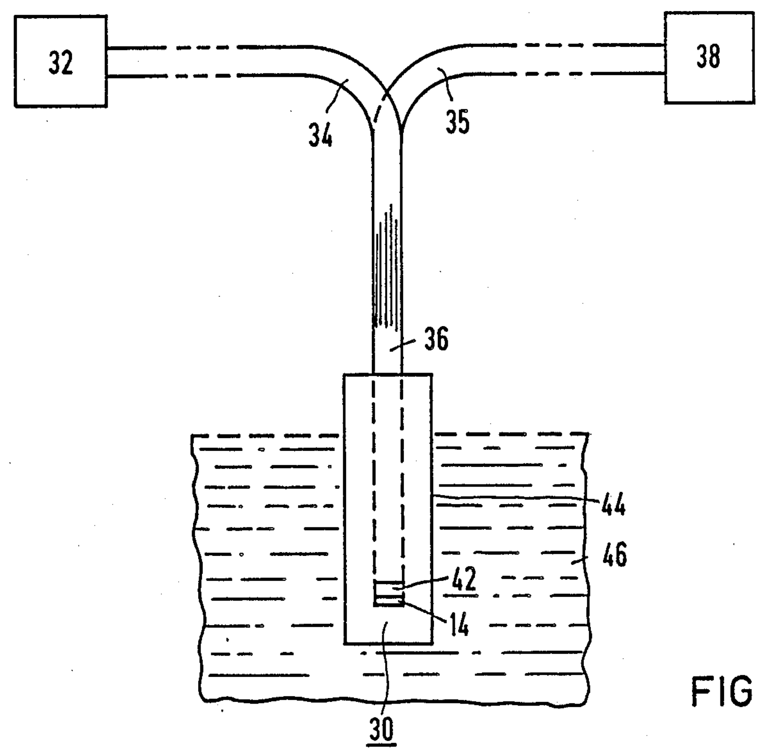
FIG. 7 shows an optical immersion sensor according to the present invention.

The optical immersion sensor embodiment of the present invention, shown in FIG. 7, to prove the existence of gases and liquids in solutions using light guide technology, comprises a light source 32, a light guide, serving as a supply line 34, a light guide serving as a return line 35, and a receiver 38. The extremities of both light guides, 34 and 35, can form a common optical fiber bundle, 36, whereby a reflector, 30 contains the sensor layer, 14, preferably provided with a carrier, 42. The end of the optical fiber bundle 36, with the reflector 30, is preferably provided with a casing 44, which serves as a membrane.

A light emitting diode (LED), preferably a laser, more preferably an impulse-commutate semiconductor laser, can be utilized as a light source 32. The light guides 34 and 35 respectively, may comprise a bundle of glass fibers, which are combined at the end to form a common glass fiber bundle 36. A portion of the glass fibers serve to supply the light beam, and the remaining portion serve to lead back the reflecting light. Reflector 30 preferably comprises a layer of a 3,3-diphenylphthalide, with a thickness of approximately 0.1 to 0.2 μm. Carrier 42 may comprise a plastic film, preferably a polyester film, having a thickness of approximately 100 μm. The casing 44 may comprise a material which allows the gas to be measured, or the vapor from the liquid to be measured, to be diffused out of the measuring solution 16 to the reflector 30. Tetrafluorethylene (Teflon), for example, has this property and is therefore suitable for casing 44.

Figure 8:
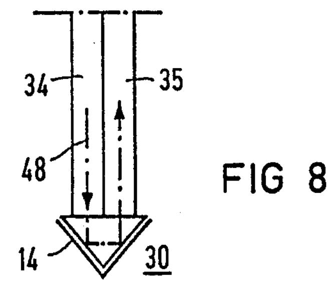
FIG. 8 shows a portion of an optical immersion sensor according to the present invention.

In another embodiment of the sensor, both light guide 34 and light guide 35 can be arranged next to each other, as shown in FIG. 8, such that the end faces of light guides 34 and 35, lie on their ends in one plane. A prism, provided with the sensor layer 14, serves as a reflector 30, and is attached to both end faces. The oncoming rays 48, in the light guide 34, indicated by a broken line in FIG. 8, are then redirected, after reflecting twice on the lateral surfaces, to the light guides 35. The reflected quantity of light changes if the transmissivity, or the color, of the reflector 30 changes under the effect of the gas.

A conical reflector can also be provided, having the end faces of both light guides 34 and 35 attached to its base, so that they lie directly next to each other. As with the prism, the covering of the conical reflector is supplied with the sensor layer 14.

We claim:

1. An apparatus for continuously measuring the partial pressure of gases or vapors with a chemically sensitive sensor material, having an electrical resistance or dielectric constant that changes in response to a change in the partial pressure of the gas or vapor, the sensor material comprising:

a dielectric material, having an ion mobility or ion concentration which changes in response to a change in the partial pressure of the gas or vapor, selected from the group consisting of a metal complex having at least one hydrophobing ligand and a mixture of at least one phthalide with at least one acidic component.

2. The apparatus of claim 1, further comprising an a stable multivibrator which converts a change in the electric resistance or the dielectric constant into a change in frequency.

3. The apparatus of claim 1, wherein the metal complex further comprises macrocyclic metal complexes.

4. The apparatus of claim 3, wherein the macrocyclic metal complex further comprises crown ether.

5. The apparatus of claim 3, wherein the macrocyclic metal complex further comprises §-benzo[15]crown-5.

6. The apparatus of claim 3, wherein the macrocyclic metal complex further comprises cryptands.

7. The apparatus of claim 6, wherein the cryptands further comprises §-benzo-cryptands.

8. The apparatus of claim 7, wherein the §-benzo-cryptands further comprise §-$222_B$.

9. The apparatus of claim 1, further comprising variably charged metal ions.

10. The apparatus of claim 9, wherein the variably charged metal ions are selected from the group consisting of sodium ion, $Na^+$; a potassium ions, $K^+$; and a magnesium ions, $Mg^{++}$.

11. The apparatus of claim 1, further comprising metal complexes with counter ions of variable nucleophiles.

12. The apparatus of claim 11, wherein the metal complexes with counter ions of variable nucleophiles are selected from the group consisting of chloride anions, $Cl^-$ and perchlorate anions, $ClO_4^-$.

13. The apparatus of claim 1, further comprising at least one protic co-substance.

14. The apparatus of claim 13, wherein the protic co-substance further comprises pyrogallol.

15. The apparatus of claim 1, further comprising at least one aprotic co-substance.

16. The apparatus of claim 1, wherein the phthalide further comprises etherfied polyethylene glycols.

17. The apparatus of claim 1, wherein the phthalide further comprises a substitute phthalide.

18. The apparatus of claim 17, wherein the substitute phthalide further comprises 3-(N-methyl-3-indolyl)-6-dimethylaminophthalide.

19. The apparatus of claim 17, wherein the substitute phthalide further comprises a 3,3-diphenylphthalide.

20. The apparatus of claim 19, wherein the 3,3-diphenylphthalide further comprises 3,3-bis(p-dimethylaminophenyl)-6-dimethylaminophthalide.

21. The apparatus of claim 19, wherein the 3,3-diphenylphthalide further comprises 3-(p-dimethylaminophenyl)-3-(p-methoxyphenyl)-6-dimethylaminophthalide.

22. The apparatus of claim 1, wherein the acidic component further comprises phenolic acids.

23. The apparatus of claim 22, wherein the phenolic acids further comprise 2,2-bis(4-hydroxyphenyl)-propane.

24. The apparatus of claim 22, wherein the phenolic acid further comprises hydroxy-(phenyl)-bis(p-hydroxyphenyl)-menthane.

25. The apparatus of claim 1, wherein the sensor material is embedded in a matrix substance.

26. The apparatus of claims 1, wherein the sensor material is arranged on one carrier.

27. The apparatus of claim 1 further comprising:

a chamber containing the sensor material and a gas permeable membrane forming at least one side of the chamber.

* * * * *